US010371670B2

(12) United States Patent
Loubet et al.

(10) Patent No.: US 10,371,670 B2
(45) Date of Patent: Aug. 6, 2019

(54) GAS CHROMATOGRAPH

(71) Applicant: ALPHA M.O.S, Toulouse (FR)

(72) Inventors: François Loubet, Avignonet-Lauragais (FR); Sébastien Pelletier, Pechabou (FR); Sandrine Isz, Toulouse (FR); Jean-Christophe Mifsud, Goudourville (FR)

(73) Assignee: ALPHA M.O.S., Toulouse (FR)

( * ) Notice: Subject to any disclaimer, the term of this patent is extended or adjusted under 35 U.S.C. 154(b) by 0 days.

(21) Appl. No.: 15/643,640

(22) Filed: Jul. 7, 2017

(65) Prior Publication Data
US 2018/0011066 A1 Jan. 11, 2018

(30) Foreign Application Priority Data

Jul. 7, 2016 (EP) .................................... 16305860

(51) Int. Cl.
G01N 30/04 (2006.01)
G01N 30/02 (2006.01)
(Continued)

(52) U.S. Cl.
CPC ........... *G01N 30/04* (2013.01); *G01N 27/125* (2013.01); *G01N 30/78* (2013.01);
(Continued)

(58) Field of Classification Search
CPC ...... G01N 30/04; G01N 27/125; G01N 30/78; G01N 33/0031; G01N 33/0047;
(Continued)

(56) References Cited

U.S. PATENT DOCUMENTS 6,455,319 B1\* 9/2002 Lewis ................. G01N 27/126
422/68.1
7,520,159 B2\* 4/2009 Paakkanen ............. B01D 53/02
73/23.35
(Continued)

FOREIGN PATENT DOCUMENTS

DE 10245947 A1 4/2004
EP 2533037 A1 12/2012
(Continued)

OTHER PUBLICATIONS

European Search Report for 16305860.5 dated Jan. 4, 2017.
(Continued)

*Primary Examiner* — Natalie Huls
*Assistant Examiner* — Suman K Nath
(74) *Attorney, Agent, or Firm* — Meagher Emanuel Laks Goldberg & Liao, LLP

(57) ABSTRACT

A hybrid device comprising Metal Oxide Sensors in a Gas Chromatography column is described, whereby the readings from the MOS devices will vary along the column in reaction to the sample reflecting the differential delays imposed on the components of the sample depending on the elutive effect of the adsorbent lining the column for the respective component. By this means, a family of readings is obtained, any one of which may be easier to interpret for a particular sample, and which may be compared amongst themselves providing an additional measurement dimension. The behavior of later sections of column or sensors may be modified dynamically during a measurement cycle depending on the readings obtained at the earlier stages.

16 Claims, 11 Drawing Sheets

(51) Int. Cl.
*G01N 30/78* (2006.01)
*G01N 33/00* (2006.01)
*G01N 27/12* (2006.01)
*G01N 30/64* (2006.01)

(52) U.S. Cl.
CPC ..... *G01N 33/0031* (2013.01); *G01N 33/0047* (2013.01); *B81B 2201/0214* (2013.01); *G01N 30/64* (2013.01); *G01N 2030/025* (2013.01)

(58) Field of Classification Search
CPC .. G01N 30/64; G01N 2030/025; G01N 30/32; G01N 30/24; G01N 30/68; G01N 2030/324; G01N 2030/685; B81B 2201/0214; B01D 53/025
USPC .............. 73/23.42, 19.02, 23.22–23.27, 73/23.35–23.41
See application file for complete search history.

(56) References Cited

U.S. PATENT DOCUMENTS 9,841,408 B2 * 12/2017 Puget .................. G01N 30/60
2014/0105790 A1 4/2014 Gaudon et al.
2015/0316523 A1 11/2015 Patolsky
2016/0282315 A1 * 9/2016 Shimizu .............. G01N 30/463

FOREIGN PATENT DOCUMENTS

WO 0078204 A2 12/2000
WO 2011154362 A1 12/2011

OTHER PUBLICATIONS

Limin Zhu et al: "Flavor anaylsis in a pharmaceutical oral solution formulation using an electronic-nose", Journal of Pharmaceutical and Biomedical Analysis, vol. 34, No. 3, Feb. 18, 2004 (Feb. 18, 2004), pp. 453-461.

Chi-Hwan Han et al "Catalytic combustion type hydrogen gas sensor using TiO2 and UV-LED" published in Sensors and Actuators B 125 (2007) 224-228.

E. Comini et al "Light enhanced gas sensing properties of indium oxide and tin dioxide sensors" published in Sensors and Actuators B 65 _(2000). 260-263.

* cited by examiner

GAS CHROMATOGRAPH

FIELD OF THE INVENTION

The present invention relates to the field of gas chromatographs, and gas chromatography.

BACKGROUND OF THE INVENTION

Gas chromatography is a standard technique in analytical chemistry for the separation of compounds in gaseous or vapour phase form, and the identification of components of such compounds.

FIG. 1 is a schematic diagram of a gas chromatograph.

As shown in FIG. 1, the gas chromatograph comprises a conduit 100, conventionally referred to as a column. This conduit 100 is provided with a column inlet 101, which itself receives a sample from sample inlet 110 and carrier inlet 120, passage through which is controlled by an inlet valve 121. At the opposite end of the conduit 100 is a column exhaust port 102. The exhaust port feeds into a chromatography detector 140 such as a flame ionisation detector or a thermal conductivity detector. The inside walls of the column 100 are lined with an adsorbent material 130. It will be appreciated that this figure is schematic in nature. In most cases, it will not be appropriate to provide a sample continuously, in which case an additional valve may be added to inlet 110. A three way valve may also be used to support selection between the carrier and the sample.

In operation, a gaseous or vapour phase sample is introduced through the sample inlet 110, and a flow of carrier gas introduced at a controlled velocity via carrier valve 121 causes the sample to be carried along the column 100. As it flows along the column, the sample will be exposed to the adsorbent material 130, which will have a varying affinity for different components of the sample, which will introduce a varying delay in the progress of different molecules along the column, depending on the composition of the adsorbent material, referred to as the eluotropic series of the adsorbent. At the exhaust port 130 the chromatography detector 140 continuously characterises the material arriving at the end of the conduit. By noting the timing of peaks in the detector readings with knowledge of the eluotropic series of the adsorbent 130, it is possible to determine the composition of the sample.

It is desired to develop gas chromatograph equipment offering improved sensitivity and capacity to discriminate between different gases.

SUMMARY OF THE INVENTION

In accordance with a first aspect, there is provided a device for characterizing a gas comprising a conduit containing one or more regions of a first adsorbent material distributed along its length, a first gas sensor at a proximal extremity of the conduit situated so as to detect at least a first molecule, a second gas sensor at a distal extremity of the conduit situated so as to detect at least a second molecule, and an inlet for introduction of the gas at said proximal end of said conduit, wherein the conduit, the first gas sensor and said second gas sensor are so disposed that a gas sample being introduced at said inlet proceeds through said first gas sensor, the conduit and the second gas sensor in sequence.

In accordance with a development of the first aspect the first gas sensor and the second gas sensor are Metal Oxide Sensor devices.

In accordance with a further development of the first aspect the first molecule and the second molecule are the same.

In accordance with a further development of the first aspect the device further comprises a second conduit between the inlet and the first gas sensor. The second conduit contains one or more regions of a second adsorbent material distributed along its length.

In accordance with a further development of the first aspect the first adsorbent material and second adsorbent material are the same.

In accordance with a further development of the first aspect the device comprises further plurality of conduit sections arranged in an alternating fashion with a corresponding plurality of further gas sensor sections, wherein all conduits and all first gas sensors are so disposed that a gas sample being introduced at the inlet proceeds sequentially through each section of conduit, and between each pair of sections of conduit, through a respective gas sensor.

In accordance with a further development of the first aspect the device further comprises heating means or cooling means adapted to control the temperature of the gas as it passes through at least one said conduit.

In accordance with a further development of the first aspect the heating means or cooling means is adapted to control the temperature of the gas individually in each of a plurality of conduits.

In accordance with a further development of the first aspect the heating means is adapted to raise the temperature of at least one conduit to a temperature sufficient to clean the adsorbent material disposed therein.

In accordance with a further development of the first aspect the device further comprises a pressure modulator (fan/pump/compressed air) adapted to control the velocity of said gas through the conduits.

In accordance with a further development of the first aspect the sensors are disposed coaxially along the conduit.

In accordance with a further development of the first aspect the sensors are disposed tangentially on an inner surface of the conduit.

In accordance with a further development of the first aspect the device is implemented as a microelectromechanical device.

In accordance with a second aspect there is provided a method of operating a device according to the first aspect, comprising the steps of injecting the gas at the inlet, recording the output of the sensors as the gas diffuses along said conduit to compile a fingerprint of said gas, comparing said fingerprint to a library of reference fingerprints corresponding to known gases, and identifying the gas as the known gas whose reference fingerprint matches the reference fingerprint most closely.

In accordance with a development of the second aspect the steps of comparing the fingerprint to a library of reference fingerprints corresponding to known gases is repeated at intervals as the gas diffuses along the conduit during the measurement cycle, and wherein the cycle is terminated once a satisfactory match is identified.

In accordance with a third aspect there is provided a method of defining a library of reference fingerprints for use in the step of comparison according to the second aspect in a specified measurement context. This method comprises the steps of:

selecting a plurality of sample gases each comprising a proportion of one or more component gases, where the plurality of sample gases comprises samples representative of each combination of component gases in the measurement context, characterising the sample gases with a device according to the first aspect, and, selecting from the characterisation of each respective sample gas one or more reference fingerprints permitting effecting discrimination of the respective sample gas from all other sample gases.

In accordance with a fourth aspect there is provided a computer program adapted to implement the method of the second or third aspect.

BRIEF DESCRIPTION OF THE DRAWINGS

The above and other features, advantages and applications of the present invention will become more apparent from the following description of embodiments thereof, given by way of non-limiting examples, and the accompanying drawings, in which.

DETAILED DESCRIPTION OF CERTAIN EMBODIMENTS

In the present text, unless the context demands otherwise; the expression "gas" will be used to designate both a specific gas species and a mixture of different gaseous species, and the general expression "characterization" will be used to designate both the process of recognizing or detecting a particular gas and the process of determining the composition of a gas. It is to be understood that references in this text to a "gas sample" generally include references to any gas which is presented to the gas sensor, whether as a discrete sample or by exposing the sensor to an ambient gaseous medium.

Figure 2:
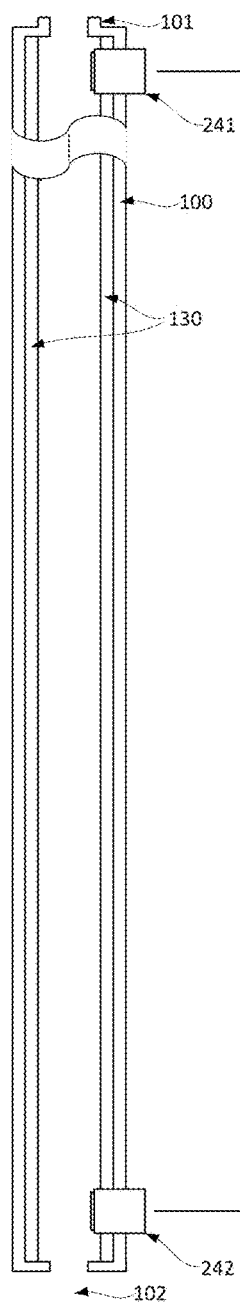
FIG. 2 shows a first embodiment.

FIG. 2 shows a first embodiment.

As shown in FIG. 2, there is provided a device for characterizing a gas comprising a conduit 100 containing one or more regions of a first adsorbent material 130 distributed along its length. The adsorbent material need not be disposed continuously along the length of the conduit, and may be of variable composition along the length of the conduit. The conduit is shown as a single straight section, but it may take the form of a meander, a spiral, a helix, a number of interconnected sections at different orientations, or any other configuration as may be appropriate, in particular in view of requirements of efficient use of space. It will be appreciated that FIG. 2 is a schematic representation, and not to any scale. In particular, the conduit 100 may be considerably longer and/or narrower than shown. Furthermore, the conduit may be excavated from a substrate rather than comprising a tube as shown, for example as a micromechanical device at a microscopic scale manufactured by lithographic or other such techniques.

The conduit may be of any phase type, for example corresponding to any of the United States Pharmacopeia phase categories. The thickness of the adsorbent film will often be determined by the physical characteristics of the chosen phase, but is not in any case constrained by the present invention.

The conduit may be of any length and diameter, bearing in mind the usual design considerations, and in particular the trade-off between shorter conduits and measurement cycles on one hand, and improved resolution and longer measurement cycles times on the other.

The carrier flow rate may similarly have any value as appropriate, bearing in mind the usual design considerations, and in particular the trade-off between shorter conduits and measurement cycles on one hand, and improved resolution and longer measurement cycles times on the other.

The device further comprises a first gas sensor 241 at a proximal extremity of the conduit 100 situated so as to detect at least a first molecule in the conduit 100, and a second gas sensor 242 at a distal extremity of said conduit 100 situated so as to detect at least a second molecule in said conduit, and an inlet 101 for introduction of the sample gas at the proximal end of the conduit 100.

In operation, a gaseous or vapour phase sample is introduced through the sample inlet 110, and a flow of carrier gas introduced at a controlled velocity via carrier valve 121 causes the sample to be carried along the conduit 100 through the first gas sensor 241, the conduit 100 and the second gas sensor 242 in sequence. The first gas sensor continuously characterises the material arriving at the inlet end of the conduit. As it flows along the column, the sample will be exposed to the adsorbent material 130, which will have a varying affinity for different components of the sample, which will introduce a varying delay in the progress of different molecules along the column, depending on the composition of the adsorbent material, referred to as the eluotropic series of the adsorbent. The second gas sensor continuously characterises the material arriving at the outlet end of the conduit.

Figure 1:
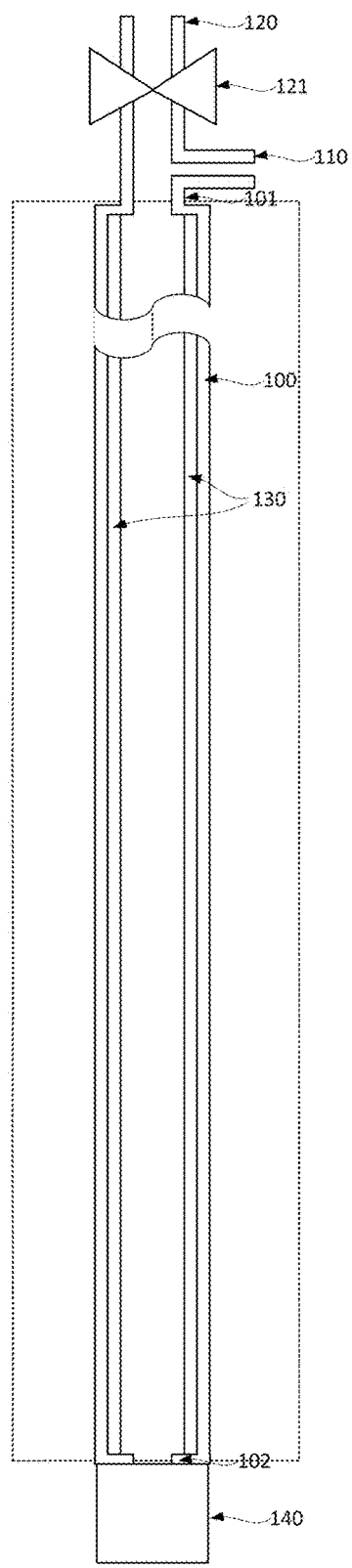
FIG. 1 is a schematic diagram of a gas chromatograph.

While in a conventional Gas Chromatograph as described with reference to FIG. 1 the identification of the sample is based on a single set of data points, by taking readings before and after elution a new dimension of characterisation is opened up, since while two samples of different compositions may give similar readings with the single sensor at the end of the conduit of FIG. 1, in many cases the comparison of signals before and after may make it possible to distinguish between such similar cases more reliably.

The first molecule detected by the first sensor and the second molecule detected by the second sensor may be the same molecule.

Gas sensors have been developed using different sensing technologies, including chemoresistor type gas sensors, such as those based on semi-conducting metal-oxides. The first gas sensor and/or the second gas sensor may be Metal Oxide Sensor devices. Metal Oxide Semiconductor devices will generally be able to detect a range of different molecules with varying degrees of certainty. Identical Metal Oxide Semiconductor devices may be used, or devices with complementary characteristics may be selected.

Further information concerning MOS devices may be found for example in "Handbook of Machine Olfaction: Electronic Nose technology" by Tim C Pearce et al. edited by John Wiley & Sons, 24 Jan. 2006 provides an introduction to the technical background in the field of the invention.

The articles "Catalytic combustion type hydrogen gas sensor using TiO2 and UV-LED" by Chi-Hwan Han et al published in Sensors and Actuators B 125 (2007) 224-228 and "Light enhanced gas sensing properties of indium oxide and tin dioxide sensors" by E. Comini et al published in Sensors and Actuators B 65_2000.260-263 may be consulted for further information concerning the state of the art.

Patent publications DE10245947 and US2014105790 are further referenced herewith.

Figure 3A:
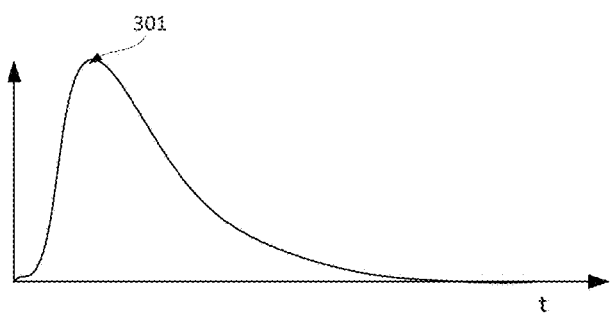
FIG. 3a shows a first hypothetical output from the first sensor.

FIG. 3a shows a first hypothetical output from the first sensor.

As shown in FIG. 3a, the sensor signal from sensor 241 is plotted on the y axis, reflecting the impedance of the MOS device, which varies in response to a higher presence of the detected molecules. This is plotted against time on the x axis, so the chart shows the evolution of impedance against time. For MOS devices, the rate of rising to a peak, and the time to fall back to a minimum is indicative of particular components in the sample. As shown here, the output curve has a single high peak 301 occurring shortly after introduction of the sample. Since at sensor 241 the sample has not been subject to any elution in the conduit 100, any time variants in the sensor response will be due to the different reaction times of the sensor to different compounds, rather than varying delays caused by differential adsorption. As such, the sensor provides data in the same way as any MOS sensor, without the additional variables introduced by gas chromatography techniques.

The curve of FIG. 3a might correspond, by way of example, to a reading obtained from a sample containing the three compounds benzene, tert-amyl alcohol & 1-butanol. For a given type of MOS sensor used in the example, these compounds are assumed to be substantially indistinguishable, producing three superposed peaks as described above.

Nevertheless, the initial sensor 241 may be used to make a preliminary characterization of the sample, so that operating conditions for the other components of the system may then be set with regard to this preliminary characterization. Furthermore, in some cases, i.e. with a different set out sample compounds, or a first MOS sensor having different characteristics, it may be possible to characterize the sample sufficiently on the basis of the output of the first sensor 241 alone, in which case the measurement process may be terminated without further delay, whereas had the first sensor been omitted, it would be necessary to complete the entire full length measurement process in every case.

Figure 3B:
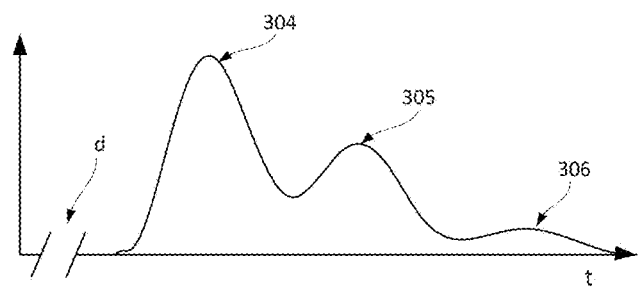
FIG. 3b shows a first hypothetical output from the second sensor.

FIG. 3b shows a first hypothetical output from the second sensor.

As shown in FIG. 3b, the sensor signal from sensor 242 is plotted on the y axis in the same way as described for FIG. 3a. The response from the MOS sensor 242 is delayed by a period d, reflecting the time taken for the sample to travel along the conduit 100 to reach the second sensor 242. As shown here, the output curve now has three distinct peaks, a high peak 304 occurring shortly after introduction of the sample, an intermediate peak 305, and third, smaller peak 306 a time late.

The fact that the three peaks have now been separated means that it is now possible to match each of the peaks to a respective component with respect to their characteristics in terms of signal shape, position or timing, retention time, surface or height, quality factor, rise time, fall time and the like in the manner of MOS sensors, and also to characterize each peak with reference to the degree of elution measurable with respect to the first curve of FIG. 3a. As such, this embodiment presents a hybrid approach combining characteristics of gas chromatography, and Metal Oxide Sensor based analyses.

Figure 4:
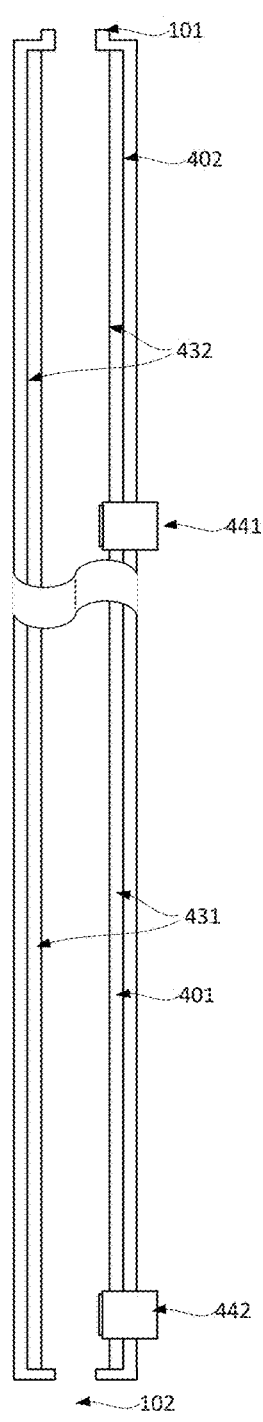
FIG. 4 shows a second embodiment.

FIG. 4 shows a second embodiment.

The embodiment of FIG. 4 is similar to that of FIG. 2, however as shown in addition to the first conduit 401 there is provided a second conduit 402 situated between the inlet 101 and the first gas sensor 441. The second conduit contains one or more regions of a second adsorbent material 432 distributed along its length correspondingly to the one or more regions of a first adsorbent material 431 distributed along the length of the first conduit 401.

By this means, each of the two sensors 441, 442 is exposed to a sample that is already the subject of elution. This may make it possible to further enhance the possibility of distinguishing between compounds which might normally give similar results.

While in certain embodiments the first adsorbent material and said second adsorbent material may be the same, by selecting different adsorbent materials for each section, it may be possible to further enhance the ability of the device to distinguish between compounds which might otherwise give similar results.

Where this approach is taken, care must be taken in selection of adsorbents, so that one adsorbent does not reverse the effects of the first, by preferentially eluting the components that were not eluted previously.

This type of issue can be avoided by simulation of different configurations at the design stage, bearing in mind the type of sample for which the device is intended.

Figure 5:
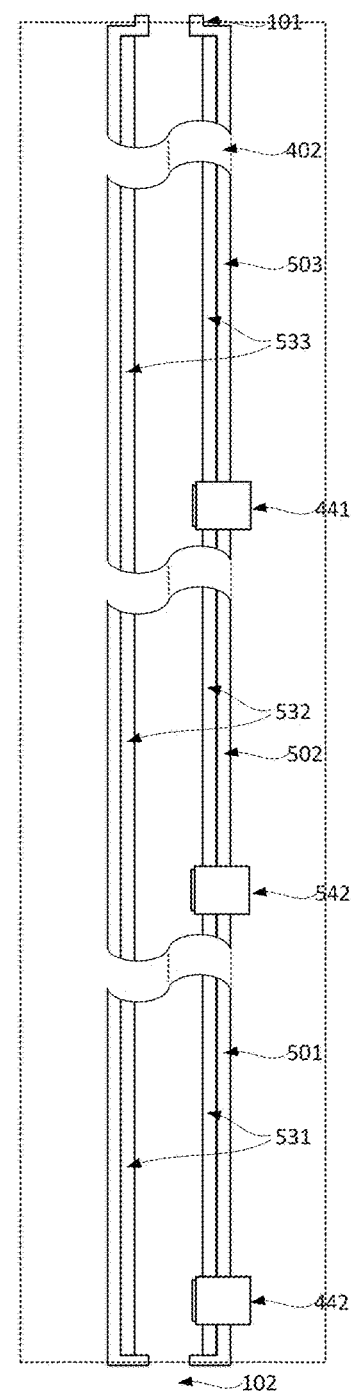
FIG. 5 shows a third embodiment.

FIG. 5 shows a third embodiment.

The embodiment of FIG. 5 is similar to that of FIG. 4, however as shown, in addition to the first conduit 501 there is provided a second conduit 502, and a third conduit 503, arranged sequentially. Each conduit has a respective adsorbent material 531, 532, 533, and a respective gas sensor 442, 542, 441. Accordingly, there is a further plurality of conduit sections arranged in an alternating fashion with a corresponding plurality of further gas sensor sections, wherein all conduits and all gas sensors are so disposed that a gas sample being introduced at said inlet proceeds sequentially through each section of conduit, and between each pair of sections of conduit, past a respective gas sensor.

It will be appreciated that any number of sections may be provided on this basis, and by the selection of complementary sensor types and adsorbent materials for each section, the device can be optimized to distinguish between a wide range of components with a high degree of certainty.

In certain embodiments, the conduit or conduits may be provided with heating means or cooling means adapted to control the temperature of the gas as it passes through that conduit. The temperature may be controlled as dictated by experimental considerations, and may be constrained by the operating characteristics of the MOS devices.

Figure 6:
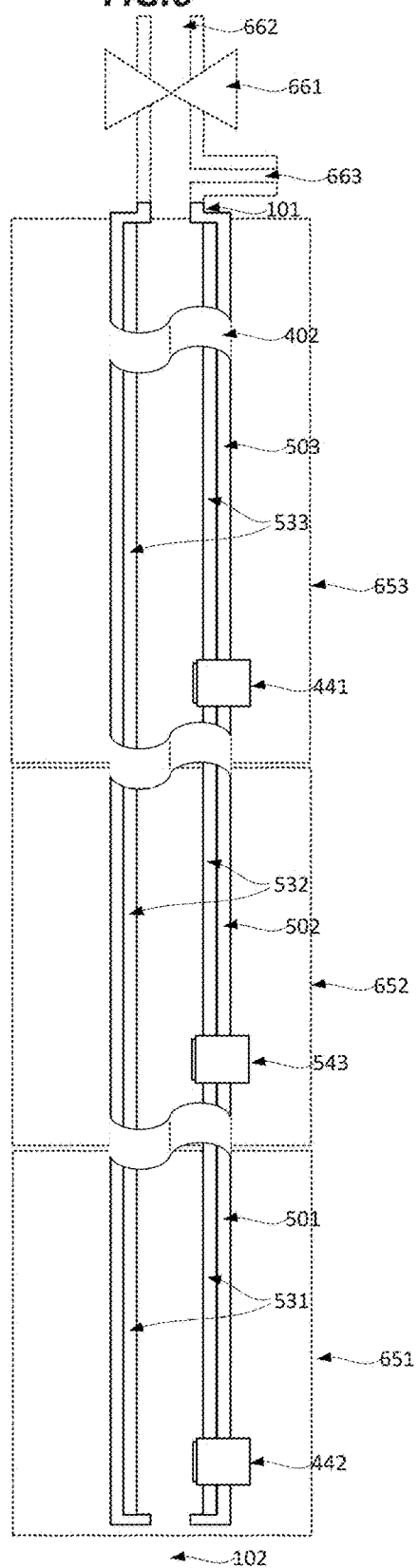
FIG. 6 shows a fourth embodiment.

FIG. 6 shows a fourth embodiment.

FIG. 6 shows a device similar to that of FIG. 5. In FIG. 6 there are additionally provided three temperature control systems 651, 652, 653, each arranged to control the temperature of gases passing through respective conduits 501, 502, 503. Since the effect of the adsorbents in each conduit is dependent on temperature, varying the temperature can improve the device's discrimination with respect to particular molecules. As such, where it proves difficult to fully characterize a particular sample, these temperature values may be modified to better distinguish between the most likely candidates, for example under programmed control as describe below. The possibility of individually controlling conduit sections can in some cases make it possible to achieve this in a single measurement cycle. It may further be noted that the behaviour of MOS devices is also temperature dependent. Conventionally the temperature of MOS devices is controlled within the device itself by means of a local heating resistance. Still further, the behaviour of the adsorbents and/or the MOS devices may be modified over time due to pollution or poisoning by sample materials. One way to remove such pollution is to raise the temperature of the adsorbent and/or MOS device above a certain temperature which will depend on the phase of the sensor. Accordingly, the temperature control systems may be adapted to raise the temperature of at least one said conduit sections to a temperature which is sufficient to clean the adsorbent material and/or sensor device disposed therein.

The embodiment of FIG. 6 further comprises a pressure modulator, schematically represented by a valve 661 and carrier gas inlet 662. In this schematic representation the carrier gas may be provided at pressure from a compressor or pressurized cylinder. In other cases, a dynamic system such as a fan or pump may perform an equivalent function, and may be situated at the input side as show, or at the output side. The sample may be sucked through the sample inlet 663, or may itself be pressurized or otherwise impelled as desired. By any of these means, or otherwise, there is provided a pressure modulator adapted to control the velocity of the gas through the conduits.

The device receives an incoming gas flow from a carrier inlet 662 and exhausts gas through exhaust 102. The inlet 662 may be supplied with a neutral carrier gas, or may simply use ambient air, or any other fluid depending on the specifics of the implementation. As shown the gas to be characterised is injected into the gas flow arriving through the inlet 101 via a sample inlet 663.

In this context, the term gas should be understood in the broadest possible sense, as discussed above or otherwise. In particular, a gas includes any sample in a substantially gaseous phase. This may include particles of solid or liquid dispersed in a gaseous carrier. This may include a gas comprising only one, or a plurality of different molecules, some or all of which may correspond to the sample to be characterised, while others may be inert or otherwise merely serve as carriers, and not to be characterised.

It should also be born in mind that the phase of matter of the sample is of significance in that it is in this phase that the sample is expected to react with the gas sensor. It is entirely possible that in parts of the system away from the gas sensor, the sample may exist in another form. In particular, the sample may circulate in a liquid, and be separated from that liquid to take a gaseous form at the relevant point by means of a semi-permeable membrane etc.

In some cases, for example where the gas to be characterised is the ambient air, the mixing of carrier and sample gases in this way may not be necessary. The pressure controller 661 may act to draw the carrier and sample gases through the inlet 101 and to impel it through the conduit 100 and out of the exhaust 102 in a controlled manner, ensuring a desired flow rate and pressure. In some implementations, for example those operating on a permanent basis, it may be desirable to ensure an airflow through the conduit whenever the gas sensor is under power, for sensor stability purposes.

It will be appreciated that while the embodiment of FIG. 6 introduces temperature control means on one hand and a pressure modulator on the other, these arrangements may be independent in operation, and that either, or both, may be combined with other embodiments as described herein or otherwise.

Figure 7:
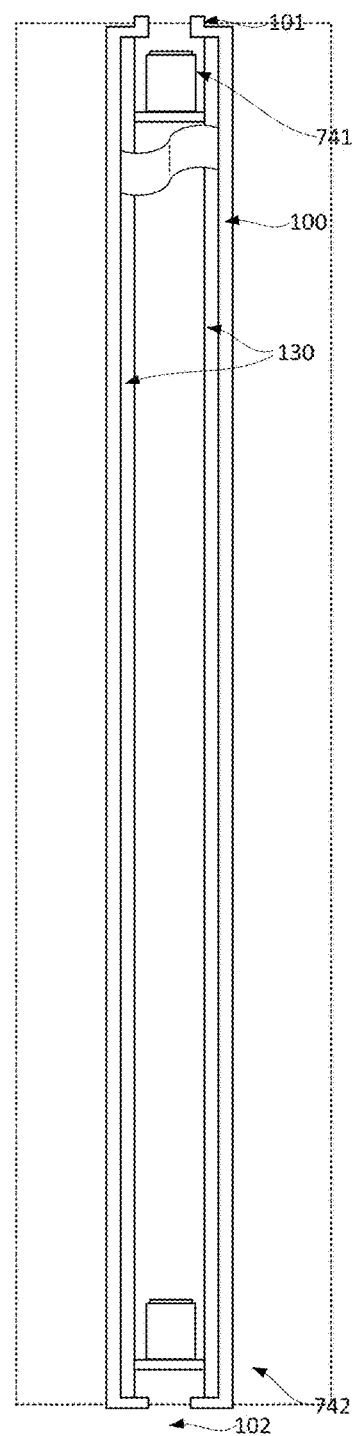
FIG. 7 shows a fifth embodiment.

FIG. 7 shows a fifth embodiment.

The embodiment of FIG. 7 is similar to that of FIG. 2, however while the sensors 241, 242 of FIG. 2 are shown as disposed tangentially on an inner surface of the conduit 100, such that the sensing surface of the sensors is in a plane substantially parallel with the axis of the conduit 100 and the direction of flow of the gas, in accordance with the embodiment of FIG. 7 the sensors 741, 742 are disposed substantially perpendicular to the flow of gas, and coaxially along the conduit 100.

This approach may offer advantages in terms of improved sensitivity, and simplified construction.

Figure 8:
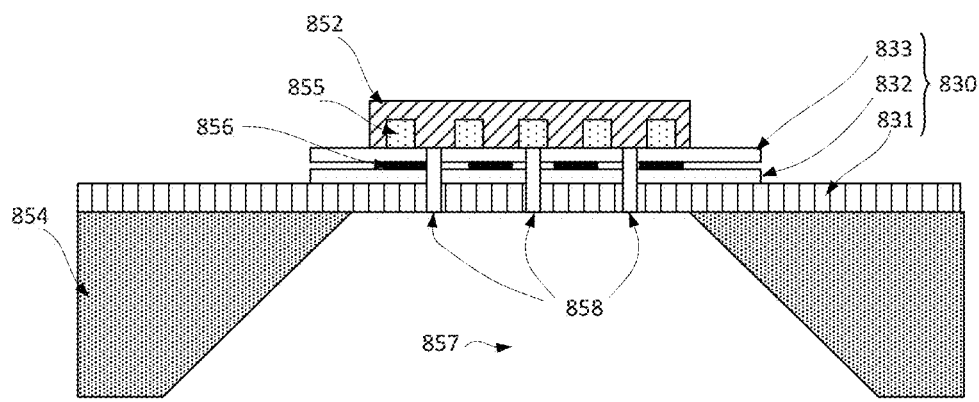
FIG. 8 illustrates a Metal Oxide Sensor structure suitable for implementation of the embodiment of FIG. 7.

FIG. 8 illustrates a Metal Oxide Sensor structure suitable for implementation of the embodiment of FIG. 7.

Each of the sensors 741, 742 may comprise one or more sensing layers 852 made of a semi-conducting metal oxide, supported on a membrane structure 830. The sensing layers may be made of various materials including, but not limited to $SnO_2$, $In_2O_3$, $ZnO$, $RuO_2$, $WO_3$, and $AB_2O_4$, (spinel type oxides); catalytic materials can also be used (alone or mixed with the oxides), such as platinum, rhodium, titanium oxide, gold, etc. Alternatively, if the sensing layer is made of a conducting polymer then it may be made of various materials including, but not limited to, polyaniline, polypyrrole, polythiophene, polyacetylene, poly(phenyl vinlene), and poly (3,4-ethylene-dioxythiphene), with any desired doping.

The present invention is not particularly limited with respect to the techniques used for deposition of the sensing material (and any catalytic material). As is well-known, the nature of the surface of the deposited sensing/catalytic material influences the efficiency of the sensor; nano-particles, and porous surfaces produced by physical vapour deposition (PVD) yield good efficiency. In general, the deposition technique will be adapted to the particular material being deposited, bearing in mind efficiency considerations. The thickness of the layer 852 will vary depending on the deposition technique and, typically, will be 100-1000 nm when PVD is used, and 10-100 µm otherwise (although these values can be varied).

As shown, the membrane structure 830 consists of three thin layers 831, 832, 833 of insulating material (for example $SiO_2$, or $Si_3N_4$, or $SiO_xN_y$, or $SiN_x$). The thin layers 832, 833 sandwich a heater and serve to isolate this heater from other components. The layer 831 functions as a membrane to support the overlying layers. Stresses in this multi-layer membrane structure can be reduced by forming the layers from different materials. In this example, layer 833 is made of $SiO_2$, layer 832 is made of $SiN_x$ and layer 831 is made of $SiO_2$.

The membrane structure 830 is mounted on a base substrate 854 which is relatively thick at the edges but has a recess 857 so as to provide a micro-hotplate structure. In the example shown, the recess 857 takes the form of an opening through the base substrate. However, the membrane structure 830 covers the opening in the base substrate 854. Typically the base substrate 854 is made from a silicon wafer because Si wafers can be machined with high precision using standard semiconductor manufacturing processes.

As illustrated holes 858 are provided through the membrane structure 830. Alternatively, the layers making up the membrane structure 830 may be porous. In this example the holes/pores 858 have a diameter of 10 μm, but other values may be envisaged, and indeed may be selected as a means for controlling the behaviour of the device as a whole.

Because the sensor has a closed type of micro-hotplate structure, and because holes 858 (or pores) are provided in registration with the sensing layers 852, gas passing through the gas sensor traverses the entire device from top to bottom.

As indicated in the previous paragraph it is advantageous to locate the holes 858 in the active area of the sensor (i.e. in registration with the sensing layer 852). However, the position of the holes 858 can be varied.

Measurement electrodes 855 are provided in contact with the respective sensing layer 852 so as to detect changes in the electrical properties of the sensing layer when it is exposed to a gas. The particular changes that take place depend on the nature of the material forming the semiconducting metal oxide and on the gaseous species present in the gas sample but, in general, consist of oxidation and/or reduction reactions changing the impedance of the sensing layer. As indicated above, in general it is necessary to heat the sensing layer in order for appreciable adsorption (and oxidation/reduction) to take place. Accordingly, a heater 856 is provided in-between the insulating layers 832, 833. The heater itself can also be used as a temperature sensor by monitoring a change of the resistance. This may not be necessary where the conduit itself is provided with temperature control means as discussed above. The sensor may also comprise a temperature sensor (not shown) so as to be able to independently monitor the temperature attained by the sensing layer 852.

In this example the measurement electrodes are made of Pt, with an underlying Ti adhesion layer, and take the form of two interlocked conductor elements having portions taking a generally circular shape.

In a similar way, in this example the heater 856 takes the form of a generally circular element which underlies the sensing layer 852. In this example the heater 856 is made of a Ti/Pt wire like the measurement electrodes, but in the case of the heater 856 the Ti/Pt wire bends back on itself to form a series of nested turns of wire. Typically the heater wire is 0.2 μm thick and 20 μm wide. Materials other than Ti/Pt, for example multilayers of refractory conductors (Mo, Ta, W, . . . ), but also polysilicon, may be used for the heater 856.

The precise positioning of the heater 856 and temperature sensor can be varied. However, the transfer of heat from the heater 856 to the sensing layer 852 is particularly efficient when the heater is provided in registration with the position of the sensing layer. In this example the heater 856 is separated from the sensing layer 852 by the membrane 833 so as to ensure electric isolation of the heater 856 from the measurement electrodes 855.

In one example using measurement electrodes 855 and a heater 856 the insulating layers 832, 833 are about 0.5 μm thick layers of $SiO_2$ and $SiN_x$, the other insulator layer 831 is about 0.8 μm thick $SiO_2$ layer and the substrate 854 is a silicon wafer of 300-500 μm thick at the edges. In this example, a sensing layer 852 made of ZnO can be brought up to a temperature of 500° C. very rapidly (in the order of 30 milliseconds for example).

In general, the sensing layer 852 is porous because it has a grain-based structure or is made of nano-particles, nano-rods, nano-wires or nano-tubes. The "Nano" prefix is conventionally considered to imply a dimension, often diameter, of less than $1 \times 10^{-7}$ M, although in the present case materials of any dimension consistent with the physical and chemical requirements of the sensor are possible. In certain embodiments the sensing layer 852 has a nano-particle structure because the ratio of surface area to volume is high for such a structure, providing a large surface area on which chemical reactions can occur with the gas under test. When the sensing layer 852 of the sensing element is exposed to a gas sample the gas will penetrate into and through the sensing layer 852 and continue along the conduit 100 because the sensing layer is porous.

In some cases the layers 833, 832, and 831 may also be traversed by holes 858 so that the gas penetrating the sensing layer 852 passes all the way through the relevant gas sensing element. The holes 858 may be made by standard processes used in semiconductor manufacture (for example using photolithography, reactive ion etching, and the like.) In a variant structure the underlying layers 833, 832, and 831 are porous and it is then not necessary to provide the holes 858. In a case where the recess 857 is spanned by a thin portion of the substrate 854, underlying the membrane structure 853, holes 858 can be provided in that substrate portion also, or it can be made of a porous material.

A plurality of such sensors may be arranged together as a network or stack, for example comprising a series of superposed sensors disposed one on top of another.

The gas passing through the sensor is modified, notably dependent on the type of oxide or conducting polymer used in the sensing layer, the temperature of the sensing layer, effects of exposure to UV radiation, if any, and the time-profile of the temperature that is applied to the sensing layer. Accordingly, the signal measured by the measurement electrodes 855 of a subsequent gas-sensing element such as in another section of conduit, or the next element in a stack, depends not only on the nature of the oxide or conducting polymer in the sensing layer of this gas sensing element, and its operating conditions (temperature, exposure to any UV radiation, time-variation in applied temperature, frequency of the voltage, voltage of sensing layer, etc.) but also on the nature of the oxide or conducting polymer in the preceding gas-sensing element and its operating conditions.

The device presented for example with reference to FIGS. 2 to 8 may implement a significant number of controllable variables, such as flow rate, temperature, voltage of sensing layer by conduit section, sensor temperature, temperature, exposure to any UV radiation, time-variation in applied temperature, frequency of the voltage, voltage of sensing layer, or any of the other variables mentioned herein, or otherwise. These variables may be controlled in a dynamic manner during the measurement cycle.

Figure 9:
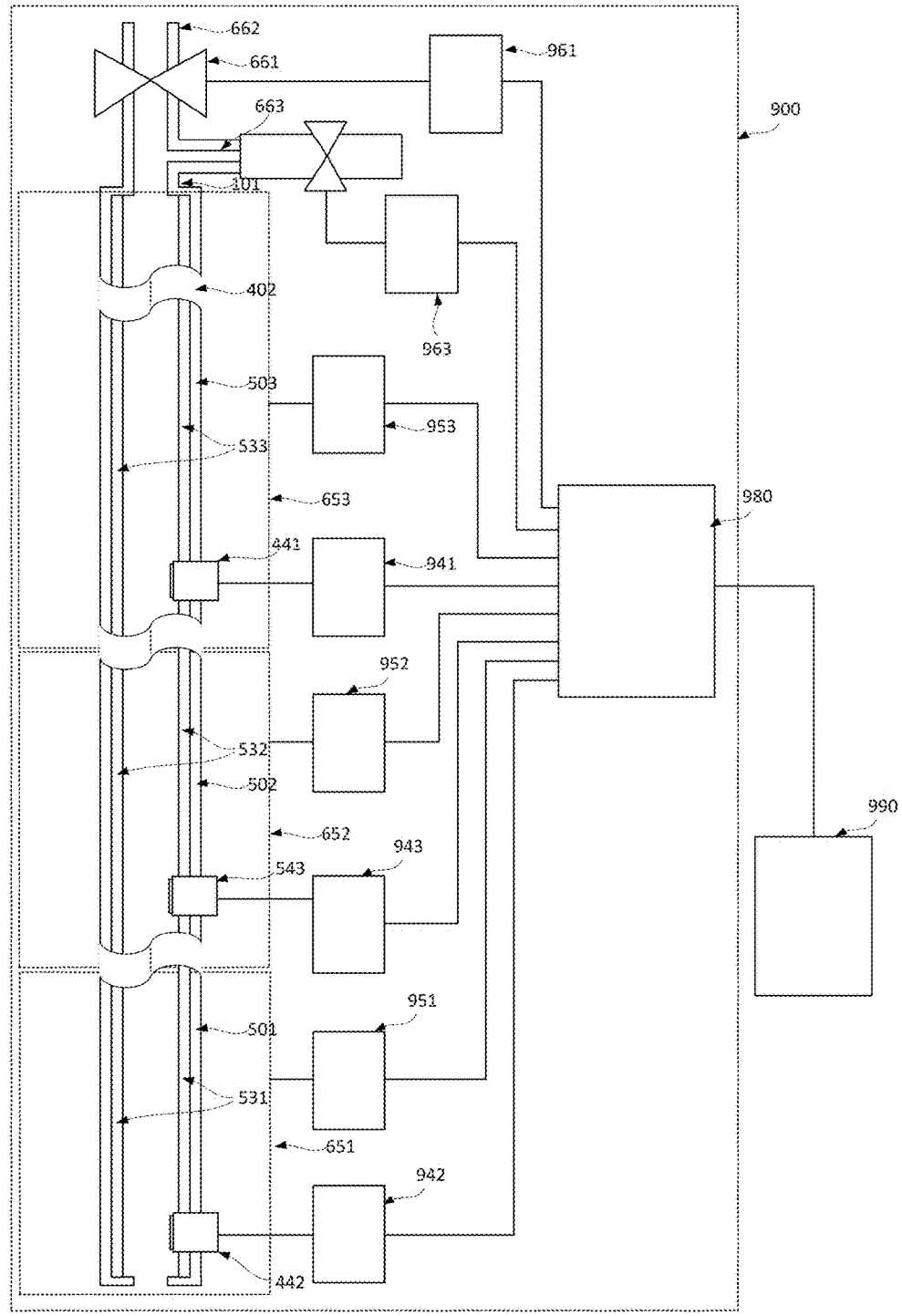
FIG. 9 shows a measurement system in accordance with an embodiment.

FIG. 9 shows a measurement system in accordance with an embodiment.

As shown in FIG. 9 there is a device similar to that described with reference to FIG. 6 above. Each of the transducers of the device of FIG. 6 is provided with a respective driver. Specifically, inlet valve 661 is read and controlled by driver 961, sample control valve 663 is read and controlled by driver 963, temperature control unit 653 is read and controlled by driver 953, sensor 441 is read and controlled by driver 941, temperature control unit 652 is read and controlled by driver 952, sensor 543 is read and controlled by driver 943, temperature control unit 651 is read and controlled by driver 951 and sensor 442 is read and controlled by driver 942. Each of the drivers 961, 963, 953, 941, 952, 943, 951, 942 is read and controlled by system controller 980, which is in turn read and controlled by processor 990.

Accordingly, the processor initiates the measurement cycle by controlling the inlet valves 661, 663 possibly triggered by a sensor sensitive to temperature, pressure, humidity, gas, or other variable as the case may be, and receives readings from the sensors 441, 442, 543. The processor may immediately start to attempt to identify the components of the sample, and depending on the developing data set, may adjust any of the system variables to better differentiate between different possible sample components.

Figure 10:
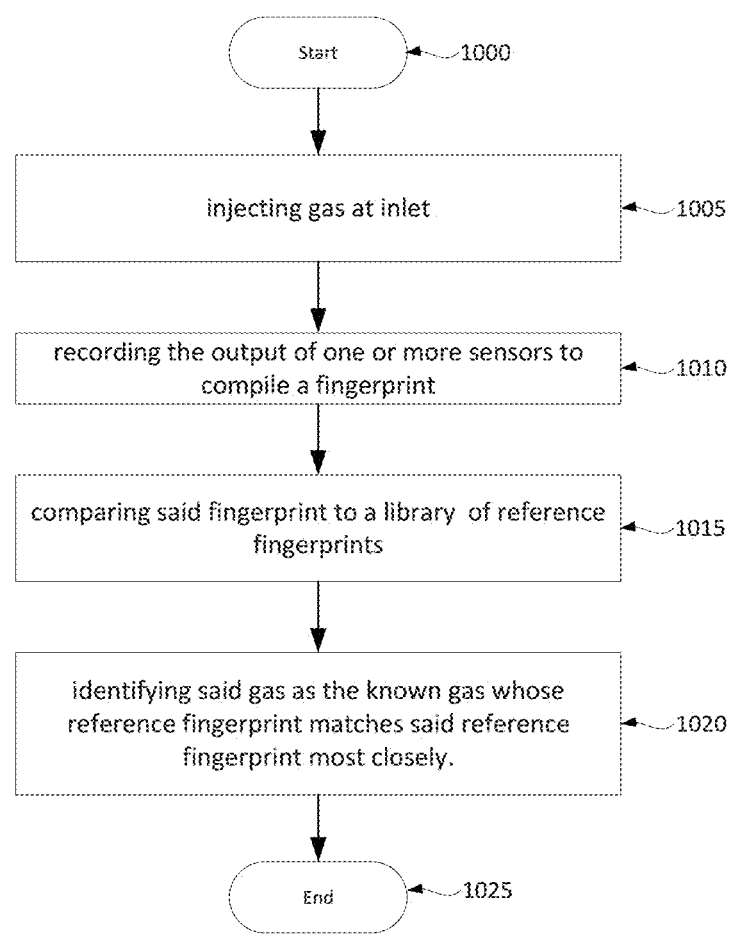
FIG. 10 shows the steps of a method in accordance with an embodiment.

FIG. 10 shows the steps of a method in accordance with an embodiment.

As shown, the method starts at step 1000 before proceeding to step 1005 at which gas is injected at the inlet. The method then proceeds to step 1010 of recording the output of one or more sensors as the gas diffuses along the conduit to compile a fingerprint of the gas. The method next proceeds to step 1015 of comparing the fingerprint to a library of reference fingerprints corresponding to known gases, and finally identifying the gas as the known gas whose reference fingerprint matches said reference fingerprint most closely at step 1020.

In some embodiments, the steps of recording and comparing may be repeated iteratively until a sufficiently close match is found at step 1020.

In some embodiments, there may be provided additional steps of determining the most likely reference fingerprint matches, and modifying system variables in a manner determined to most clearly distinguish between those most likely matches.

In some embodiments, the steps of recording and comparing may be terminated once a satisfactory match is identified, that is to say, without waiting for the sample to reach the last or any particular sensor in the conduit.

Still further, the operating conditions of the sensors or conduit sections may be dynamically set during a sample cycle. In particular, measurements at the first or earlier sensors may be used to determine the settings at later sensors and/or conduit sections most appropriate to the detected sample and most apt to enable discrimination between the most likely components of the detected sample, as predicted on the basis of the initial measurements.

Still further, the sections of conduit need not be arranged in a simply linear fashion—there may be provided one or more branches at different stages of the conduit. Respective branches may be provided with different adsorbent materials, so that the behaviour of the sample gas in different conditions of elution may be monitored and compared. Some or all of these branches may be controlled by valves, such that the path of the sample through the different sections is controlled dynamically, so that as the measurement cycle progresses, different adsorbents may be determined to be useful in clarifying the results of earlier sections.

Still further, more than one sensor may be provided at the same position along the conduit. These sensors may have different characteristics such that depending on the sample to be characterised, the readings from different sensors may be accorded more or less importance.

In addition to sampling the outputs of the various drivers and sensors to compile the sample fingerprint, the system may process the sampled information to further characterise the readings, for example by extracting peak values, time to rise to a particular value, or to a peak value, time to rise to a specified proportion of a peak value, time to fall to zero from a peak value, time to fall to a specified proportion of a peak value, time to fall to a specified value, time to fall to zero, peak rise rate, rise rate at a specified point in the measurement cycle, peak fall rate, fall rate as a specified point in the measurement cycle, etc. The system may calculate mean values, standard deviations or other statistical evaluations. The system may perform curve fitting or regression analysis, noise reduction, signal processing transform and baseline adjustment. Instructions specifying which such calculations are to be performed on the basis of which measurements may be incorporated in the measurement protocol.

As such, the final sample fingerprint may comprise raw reading data, processed representations of the sample data or a combination of both.

In certain embodiments, the library of reference fingerprints used at step 1015 may itself be selected dynamically. In such cases, once the sample fingerprint is available, the processor 990 may select a library from memory. The library may be selected on the basis of any available information about the type of sample being characterised, and the ambient conditions in place at the time of the measurement cycle. This may involve user input in order to provide any available information about the sample—for example, the user might specify that the sample was a particular foodstuff type, which may then provide a basis for preferentially selecting certain characterisation libraries. Alternatively, the system may communicate with other devices to obtain relevant information—for example, a connected refrigerator may be able to provide information about its contents, or product packaging may have bar codes, RFID tags or other identifiers that can be used to retrieve additional information concerning the sample. Different libraries may in some cases be applicable depending on the readings of ambient conditions such as temperature, pressure and humidity.

Each characterisation library comprises a plurality of reference fingerprints. A reference fingerprint is a representative set of data corresponding to the data in the sample fingerprint, together with classification data. Reference fingerprints may be provided representative of different subcategories of the type of sample under study. For example if the sample type is "Coffees", a characterisation target may be provided for each combination of multidimensional characteristics that may classify a particular sample (species, origin, condition, taste profile, quality, etc.), or alternatively, separate characterisation may be provided for each dimension, which may be applied separately to the sample characterisation, and combined to provide the final complete classification of the sample.

The comparison process may be carried out by means of multivariate analysis techniques such as k-NN (k-Nearest Neighbour), CA (Cluster Analysis), DFA (Discriminant Function Analysis), PCA (Principal Component Analysis), PCR (Principal Component Regression) Multiple Linear Regression (MLR), hierarchical cluster analysis (HCA), ANN (Artificial Neural Networks), Fuzzy-ART, PNN (Probabilistic Neural Network), LVQ (Learning Vector Quantization), SOM (Self Organizing Map) and so on. The analysis may also make use of neural network and fuzzy logic technologies, such as Back Propagation, Multilayer perceptron, Radial Basis Function, Adaptive Resonance Theory, and the like.

Accordingly, there is provided a method of defining a library of reference fingerprints for use in comparison as described above, in particular with reference to step 1015 of the method described with regard to FIG. 10 in a specified measurement context. In this sense a specified measurement context may be defined primarily in terms of the type of sample to be tested, such as coffees.

The method comprises the further step of selecting a plurality of sample gases each comprising a proportion of one or more component gases, where the plurality of sample gases comprising samples representative of each combination of component gases in said measurement context. The identities of the component gases, or their respective proportions may or may not be known. As such, the set of sample gases may generally comprise every gas that may plausibly or probably occur in the measurement context. This may imply the determination of a level of granularity, dictating how many levels of sub category should be distinguished. In this context, the term gas is of course understood in the broad terms presented above, and may in fact comprise the vapours emanated by physical samples.

The method further comprises the step of characterising each sample gases with a device as described above, for example with respect to any of FIGS. 2, 4, 5, 6, 7, 9 or otherwise. Generally the characterisation will be limited to numerical measurements of the different output by the devices under different operating conditions, since at this stage it may be that characterisation is performed without reference to a characterisation library. Alternatively, characterisation may be performed with the benefit of a characterisation library as described with reference to FIG. 10, for example where a characterisation library is available for a more general case than the library under preparation such as a broader category which includes the current measurement context, or for a parallel case such as a different category of samples which may be expected to have partially comparable characteristics, or for a narrower category, which constitutes a part of the current measurement context. A number of such libraries may be used together, and further supplemented by merely numerical or qualitative information. To provide the richest characterisation set possible, the device may cycle through different permutations of the different possible operating conditions such as flow rate, temperature, and so on. In cases where the device is provided with multiple sensors at the same point along the conduit, or multiple paths through the conduits, measurements may be performed by multiple arrangements of sensors and/or conduits.

The reference fingerprints might be sensor responses but also characteristic derivative values due to the temperature modulation for example, such as Reaction Start Time (RST), Recovery Time, Delay time (the delay between the response of different sensors, where applicable), response inflection point, signal processing transform, etc.

This process will provide a multidimensional matrix opposing x readings (response at fixed time intervals for example) versus y samples.

The method finally comprises selecting from the characterisation of each respective sample gas one or more reference fingerprints permitting effective discrimination of the respective sample gas from all other said sample gases.

This matrix will often be large, but a variety of algorithms are known for the identification of critical variable and characteristic results enabling the quantification of a gas and discrimination of samples, for the range outlined by the set of representative samples. Such algorithms may include multivariate analysis techniques such as k-NN (k-Nearest Neighbour), CA (Cluster Analysis), DFA (Discriminant Function Analysis), PCA (Principal Component Analysis), PLS (Partial Least Square), PCR (Principal Component Regression) Multiple Linear Regression (MLR), hierarchical cluster analysis (HCA), ANN (Artificial Neural Networks), Fuzzy-ART, PNN (Probabilistic Neural Network), LVQ (Learning Vector Quantization), SOM (Self Organizing Map) and so on.

Libraries may be downloaded from a remote server on demand, and certain activities may be carried out either locally or remotely.

In certain embodiments there is accordingly provided a hybrid device comprising Metal Oxide Sensors in a gas chromatography column is described, whereby the readings from the MOS devices will vary along the column in reaction to the sample reflecting the differential delays imposed on the components of the sample depending on the elutive effect of the adsorbent lining the column for the respective component. By this means, a family of readings is obtained, any one of which may be easier to interpret for a particular sample, and which may be compared amongst themselves providing an additional measurement dimension. The behaviour of later sections of column or sensors may be modified dynamically during a measurement cycle depending on the readings obtained at the earlier stages.

The disclosed methods can take form of an entirely hardware embodiment (e.g. FPGA), an entirely software embodiment (for example to control a system according to the invention) or an embodiment containing both hardware and software elements. Software embodiments include but are not limited to firmware, resident software, microcode, etc. The invention can take the form of a computer program product accessible from a computer-usable or computer-readable medium providing program code for use by or in connection with a computer or an instruction execution system. A computer-usable or computer-readable can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

These methods and processes may be implemented by means of computer-application programs or services, an application-programming interface (API), a library, and/or other computer-program product, or any combination of such entities.

Figure 11:
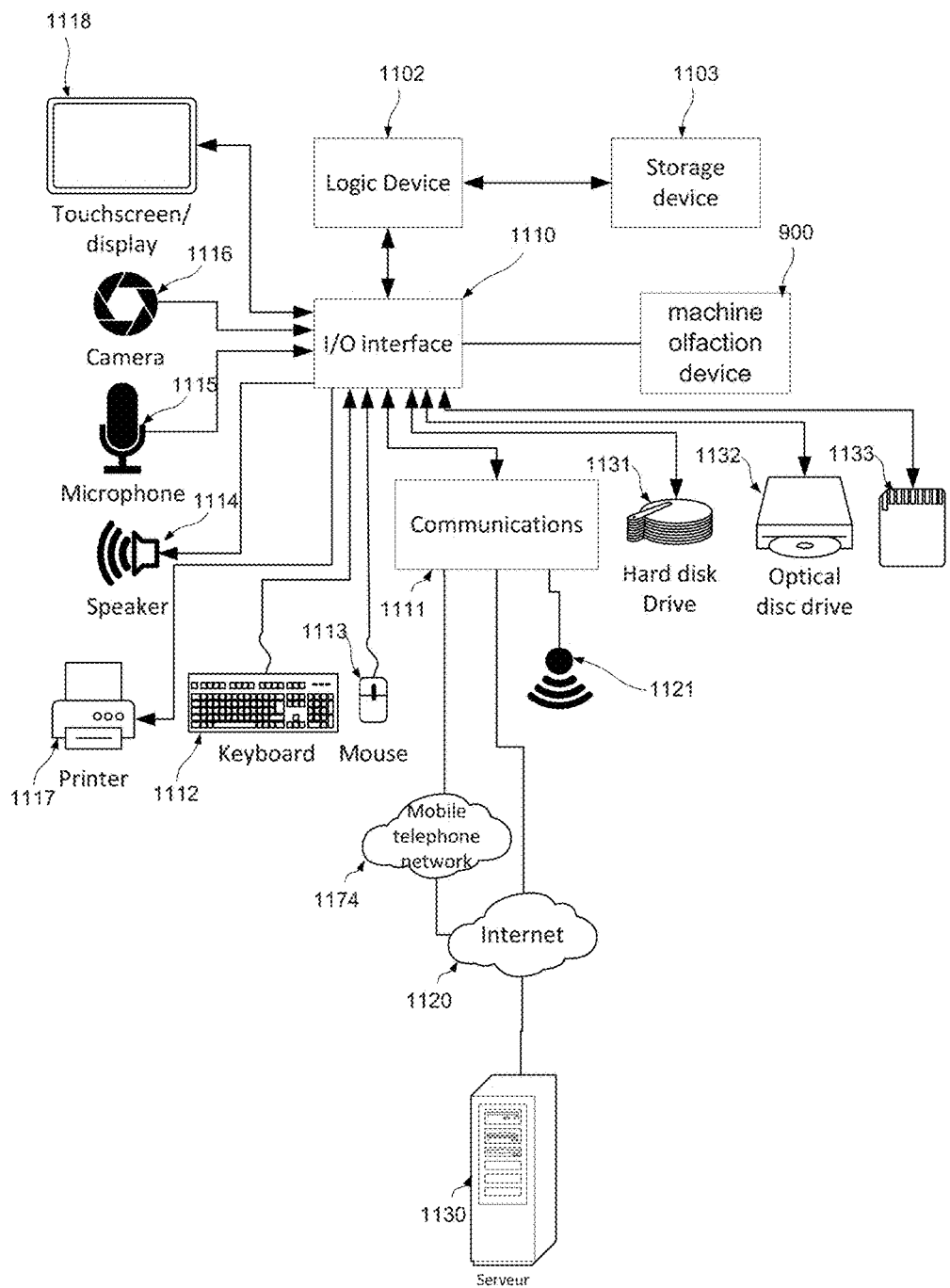
FIG. 11 shows a generic computing system suitable for implementation of embodiments of the invention.

FIG. 11 shows a generic computing system suitable for implementation of embodiments of the invention.

A shown in FIG. 11, a system includes a logic device 1102 and a storage device 1103. The system may optionally include a display subsystem 1118, input/output subsystem 1110, communication subsystem 1111, and/or other components not shown. Logic device 1102 includes one or more physical devices configured to execute instructions. For example, the logic device 1102 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 1102 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 1102 optionally may be distributed among two or more separate devices, which may be remotely located and/or configured for coordinated processing. Aspects of the logic device 1102 may be virtualized and executed by remotely accessible, networked computing devices configured in a cloud-computing configuration.

Storage device 1103 includes one or more physical devices configured to hold instructions executable by the logic device to implement the methods and processes described herein. When such methods and processes are implemented, the state of storage device 1103 may be transformed—e.g., to hold different data.

Storage device 1103 may include removable and/or built-in devices. Storage device 1103 may comprise one or more types of storage device including optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device may include volatile, non-volatile, dynamic, static, read/write, read-only, random-access, sequential-access, location-addressable, file-addressable, and/or content-addressable devices.

In certain arrangements, the system may comprise an interface 1110 adapted to support communications between the Logic device 1102 and further system components, in particular the machine olfaction device 900. In such an arrangement, the system comprising the logic device 1102, storage device 1103 and I/O interface 1110 may fulfil the role of the processor 990 described above.

For example, additional system components may comprise removable and/or built-in extended storage devices. Extended storage devices may comprise one or more types of storage device including optical memory 1132 (e.g., CD, DVD, HD-DVD, Blu-Ray Disc, etc.), semiconductor memory 1133 (e.g., RAM, EPROM, EEPROM, FLASH etc.), and/or magnetic memory 1131 (e.g., hard-disk drive, floppy-disk drive, tape drive, MRAM, etc.), among others. Such extended storage device may include volatile, non-volatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 1102 and storage device 1103 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

In particular, the system of FIG. 11 may be used to implement embodiments of the invention.

For example a program such as one implementing the steps described with respect to FIG. 10 may be stored in storage device 1103 and executed by logic device 1102. Furthermore, a program such as one implementing the generation of a characterisation library as described above may be stored in storage device 1103 and executed by logic device 1102. The communications interface 1111 may receive Characterisation Libraries from the characterization server 1130, and upload sample type information or sample characterization data as discussed above. The Logic device 1102 may receive and compile the sample characterization, perform any additional processing, compare the final sample characterization with the characterization library, and report the results to the user via display 1118. At various stages of the operation further inputs, for example concerning the sample type, may be prompted via the display 1118, and recovered via the user input interface devices 1116, 1115, 1114, 1113, 1112 as described below under the control of a suitable program, or may interface with internal or external dedicated systems adapted to perform some or all of these processes.

Accordingly the invention may be embodied in the form of a computer program.

It will be appreciated that a "service", as used herein, is an application program executable across multiple user sessions. A service may be available to one or more system components, programs, and/or other services. In some implementations, a service may run on one or more server-computing devices.

When included, display subsystem 1118 may be used to present a visual representation of data held by storage device. This visual representation may take the form of a graphical user interface (GUI). As the herein described methods and processes change the data held by the storage device 1103, and thus transform the state of the storage device 1103, the state of display subsystem 1118 may likewise be transformed to visually represent changes in the underlying data. Display subsystem 1118 may include one or more display devices utilizing virtually any type of technology. Such display devices may be combined with logic device and/or storage device in a shared enclosure, or such display devices may be peripheral display devices.

When included, input/output subsystem 1110 may comprise or interface with one or more user-input devices such as a keyboard 1112, mouse 1113, speaker 1114, Microphone 1115, camera 1116, printer 1117, display or touch screen 1118, near field communications interface 1121, or game controller (not shown). In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, colour, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1111 may be configured to communicatively couple computing system with one or more other computing devices. For example, communication module of may communicatively couple computing device to remote service hosted for example on a remote server 1130 via a network of any size including for example a personal area network, local area network, wide area network, or the internet. Communication subsystem may include wired and/or wireless communication devices compatible with one or more different communication protocols. As non-limiting examples, the communication subsystem may be configured for communication via a wireless telephone network 1174, or a wired or wireless local- or wide-area network. In some embodiments, the communication subsystem may allow computing system to send and/or receive messages to and/or from other devices via a network such as the Internet 1120. The communications subsystem may additionally support short range inductive communications 1121 with passive devices (NFC, RFID etc).

Figure 12:
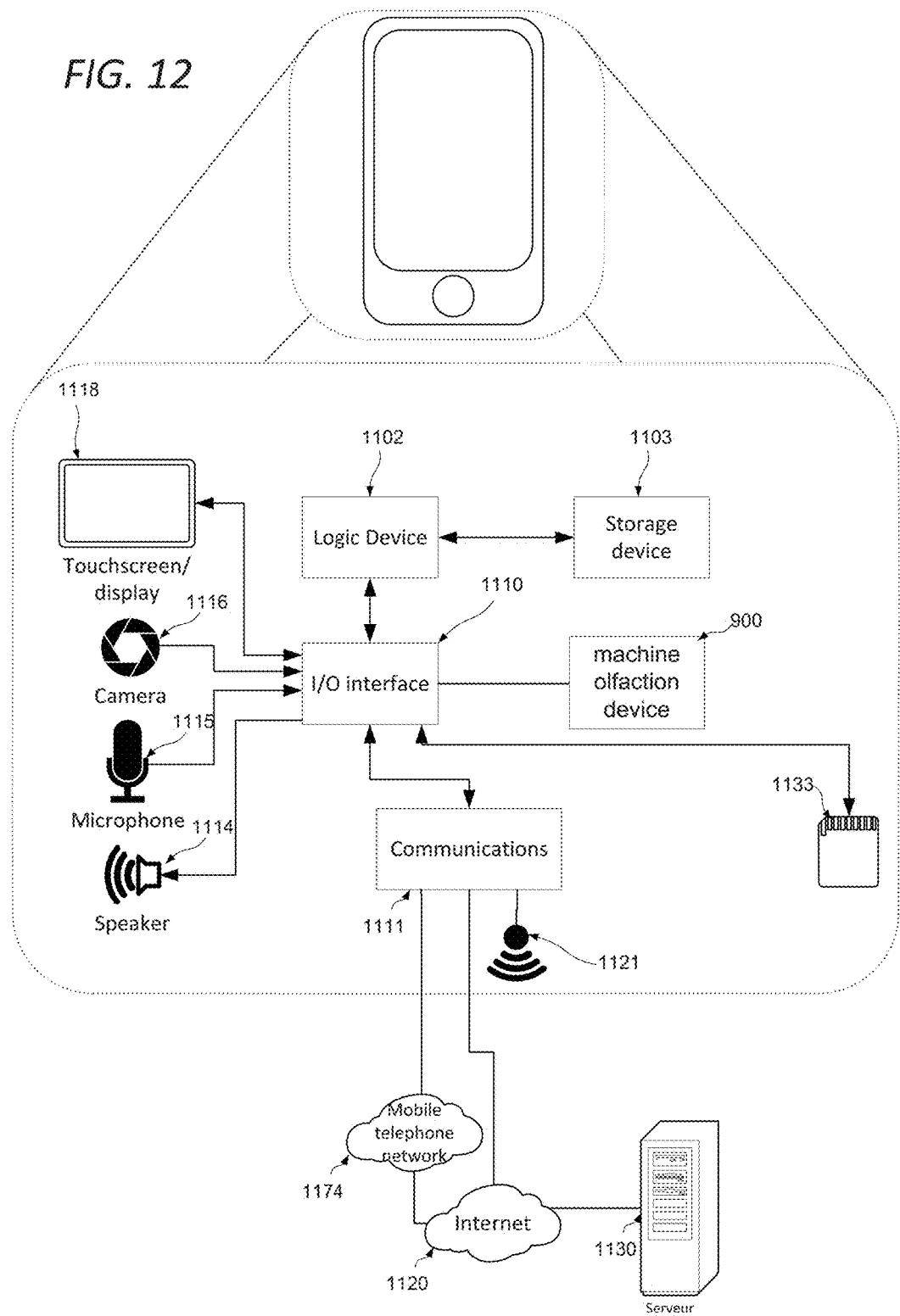
FIG. 12 shows a smartphone device adaptable to constitute an embodiment.
Figure 13:
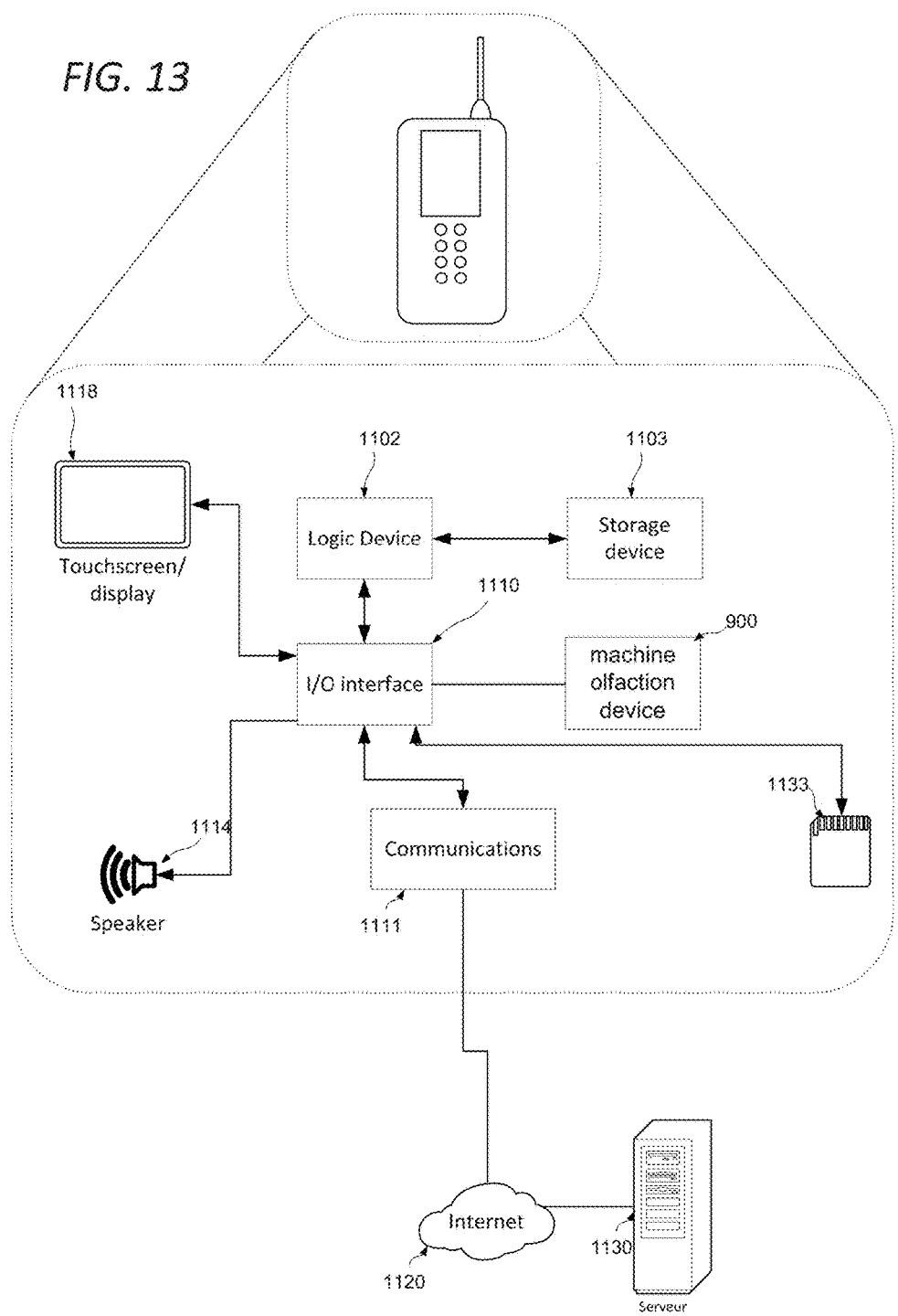
FIG. 13 shows a hand scanner device adaptable to constitute an embodiment.
Figure 14:
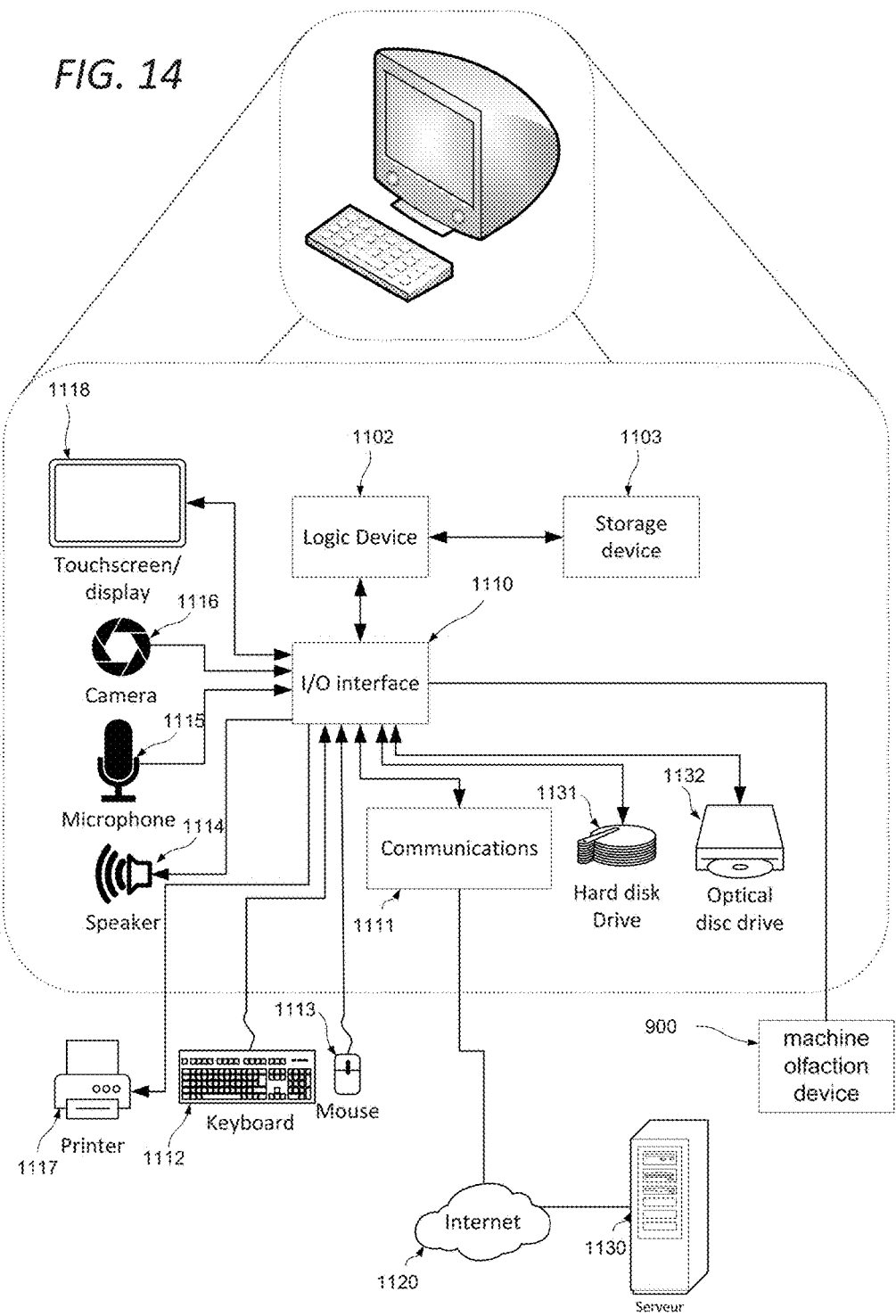
FIG. 14 shows a desktop computer device adaptable to constitute an embodiment.

The system of FIG. 11 is intended to reflect a broad range of different types of information handling system. It will be appreciated that many of the subsystems and features described with respect to FIG. 11 are not required for implementation of the invention, but are included to more realistically reflect common systems. It will be appreciated that system architectures vary widely, and the relationship between the different sub-systems of FIG. 11 is merely schematic, and is likely to vary in terms of layout and the distribution of roles in real systems. It will be appreciated that in practice, systems are likely to incorporate different subsets of the various features and subsystems described with respect to FIG. 11. FIGS. 12, 13 and 14 discuss in further detail some common example devices.

FIG. 12 shows a smartphone device adaptable to constitute an embodiment. As shown in FIG. 12, the smartphone device incorporates elements 1102, 1103, 1111, 900, 1116, 1115, 1114, 1118, 1111, 1121 and 1133 as described above. It is in communication with the telephone network 1174 and a server 1130 via the network 1120.

FIG. 13 shows a hand scanner device adaptable to constitute an embodiment. As shown in FIG. 13, the hand scanner device incorporates elements 1102, 1103, 1110, 900, 1118, 1111, 1114, 1133, 1120 and 1130 as described above. It is in communication with a server 1130 via the network 1120.

FIG. 14 shows a desktop computer device adaptable to constitute an embodiment. As shown in FIG. 14, the desktop computer device incorporates elements 1102, 1103, 1110, 1118, 1111, 1117, 1116, 1115, 1114, 1113, 1112, 1131 and 1132 as described above. It is in communication with elements 1117, 1112, 1113 and 900 as peripheral devices, and with a server 1130 via the network 1120.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A device for characterizing a gas, said device comprising:
    a gas chromatograph column comprising a conduit containing one or more regions of a first adsorbent material distributed along its length;
    a first MOS gas sensor at a proximal extremity of said conduit situated so as to detect at least a first molecule in said conduit;
    a second MOS gas sensor at a distal extremity of said conduit situated so as to detect at least a second molecule in said conduit;
    at least one said region of said first adsorbent material being situated between said first MOS gas sensor and said second MOS gas sensor; and
    an inlet for introduction of said gas at said proximal extremity of said conduit, wherein said conduit, said first MOS gas sensor and said second MOS gas sensor are so disposed that a gas sample being introduced at said inlet proceeds through said first MOS gas sensor, said conduit and said second MOS gas sensor in sequence, and wherein
    said device being adapted to record the output of said first MOS gas sensor and said second MOS gas sensor as said gas diffuses along said conduit to compile a fingerprint of said gas, and to obtain an identification of said gas based on a comparison of said fingerprint to a library of reference fingerprints corresponding to known gases, where said gas is identified as the known gas whose reference fingerprint matches said reference fingerprint most closely.

2. The device of claim 1 wherein said first molecule and said second molecule are the same.

3. The device of claim 1 comprising a second conduit between said inlet and said first MOS gas sensor, said second conduit containing one or more regions of a second adsorbent material distributed along its length.

4. The device of claim 3 wherein said first adsorbent material and said second adsorbent material are the same.

5. The device of claim 1 comprising a further plurality of conduit sections arranged in an alternating fashion with a corresponding plurality of further gas sensor sections, wherein all said conduits and all said first gas MOS sensors are so disposed that a gas sample being introduced at said inlet proceeds sequentially through each section of conduit, and between each pair of sections of conduit, through a respective gas sensor.

6. The device of claim 1 further comprising heating means or cooling means adapted to control the temperature of the gas as it passes through at least one said conduit.

7. The device of claim 6 wherein said heating means or cooling means is adapted to control the temperature of the gas individually in each of a plurality of said conduits.

8. The device of claim 6 wherein said heating means is adapted to raise the temperature of at least one said conduit to a temperature sufficient to clean the adsorbent material disposed therein.

9. The device of claim 1 further comprising a pressure modulator adapted to control the velocity of said gas through said conduits.

10. The device of claim 1 wherein said MOS gas sensors are disposed coaxially along said conduit.

11. The device of claim 1 wherein said MOS gas sensors are disposed tangentially on an inner surface of said conduit.

12. The device of claim 11 wherein said device is implemented as a microelectromechanical device.

13. A method of operating the device of claim 1, said method comprising injecting said gas at said inlet, recording the output of one or more said MOS gas sensors as said gas diffuses along said conduit to compile a fingerprint of said gas, comparing said fingerprint to a library of reference fingerprints corresponding to known gases, and identifying said gas as the known gas whose reference fingerprint matches said reference fingerprint most closely.

14. The method of claim 13, wherein said comparing said fingerprint to a library of reference fingerprints corresponding to known gases is repeated at intervals as said gas diffuses along said conduit during the measurement cycle, and wherein the cycle is terminated once a satisfactory match is identified.

15. A method of defining said library of reference fingerprints for use in the method of claim 13, comprising:
- selecting a plurality of sample gases each comprising a proportion of one or more component gases, said plurality of sample gases comprising samples representative of each combination of component gases in said measurement context,
- characterising said plurality of sample gases with a device as defined in claim 1, and
- selecting from the characterisation of each respective sample gas one or more reference fingerprints permitting effective discrimination of said respective sample gas from all other said sample gases.

16. A computer program product comprising computing instructions stored in a non-transitory computer program storage medium adapted to implement the method of claim 13 when said computing instruction are executed by at least one processor.

* * * * *

UNITED STATES PATENT AND TRADEMARK OFFICE
CERTIFICATE OF CORRECTION

PATENT NO.         : 10,371,670 B2
APPLICATION NO.    : 15/643640
DATED              : August 6, 2019
INVENTOR(S)        : François Loubet et al.

Page 1 of 1

It is certified that error appears in the above-identified patent and that said Letters Patent is hereby corrected as shown below:

In the Claims

Claim 15, Column 19, Lines 18-19, delete "with a device as defined in claim 1".

Signed and Sealed this
Twenty-ninth Day of October, 2019

Andrei Iancu
*Director of the United States Patent and Trademark Office*